United States Patent [19]
Watkins et al.

[11] Patent Number: 5,769,790
[45] Date of Patent: Jun. 23, 1998

[54] FOCUSED ULTRASOUND SURGERY SYSTEM GUIDED BY ULTRASOUND IMAGING

[75] Inventors: Ronald Dean Watkins, Niskayuna; Christopher Mark William Daft, Schenectady, both of N.Y.

[73] Assignee: General Electric Company, Schenectady, N.Y.

[21] Appl. No.: 738,207

[22] Filed: Oct. 25, 1996

[51] Int. Cl.[6] .................................................. A61B 8/00
[52] U.S. Cl. .............................................. 600/439; 601/3
[58] Field of Search .................. 601/2, 3, 4; 128/662.06, 128/660.03; 600/439, 471, 2, 3; 606/1; 604/22

[56] References Cited

U.S. PATENT DOCUMENTS

| | | | |
|---|---|---|---|
| 4,757,820 | 7/1988 | Itoh | 128/660.03 |
| 4,932,414 | 6/1990 | Coleman et al. | 128/660.03 |
| 5,117,832 | 6/1992 | Sanghvi et al. | 128/662.03 |
| 5,247,935 | 9/1993 | Cline et al. | 128/653.2 |
| 5,275,165 | 1/1994 | Ettinger et al. | 128/653.2 |
| 5,291,890 | 3/1994 | Cline et al. | 128/653.2 |
| 5,307,816 | 5/1994 | Hashimoto et al. | 128/662.06 |
| 5,368,032 | 11/1994 | Cline et al. | 128/653.2 |
| 5,435,311 | 7/1995 | Umemura et al. | 601/3 X |
| 5,471,988 | 12/1995 | Fujio et al. | 128/660.03 |
| 5,492,126 | 2/1996 | Hennige et al. | 128/662.06 |
| 5,526,815 | 6/1996 | Granz et al. | 128/660.03 |
| 5,558,092 | 9/1996 | Unger et al. | 601/3 X |
| 5,573,497 | 11/1996 | Chapelon | 601/2 |

OTHER PUBLICATIONS

"Magnetic Resonance–Guided Thermal Surgery", Cline et al., Magnetic Resonance in Medicine, vol. 30, 98–106 (1993).
"One–Dimensional NMR Thermal Mapping of Focused Ultrasound Surgery" J. Computer Assisted Tomography, vol. 18, No. 3, 476–483 (1994).
"MR–Guided Focused Ultrasound Surgery", Cline et al., J. Computer Assisted Tomography, vol. 16, No. 6, 956–965 (1992).

*Primary Examiner*—Francis Jaworski
*Attorney, Agent, or Firm*—Marvin Snyder; Douglas E. Stoner

[57] ABSTRACT

A system employing ultrasound imaging as a method to localize a patient's tissue volume to be treated prior to applying therapeutic levels of ultrasound energy includes a therapy transducer for producing high-intensity fields that cause necrosis and an imaging transducer for producing high-quality ultrasound images. The therapy transducer is a spheroidal piezoelectric element and the imaging transducer is made up of a plurality of piezoelectric elements mounted in fixed relationship to the therapy transducer. The therapy transducer transmits a beam that is focused at a location in the tissue to be treated. The imaging transducer is then steered to produce successive receive beams which scan the tissue, including the tissue at the focal point of the pulsed therapy transducer. The image of the focal point is then superimposed on an image of the tissue to be treated obtained by B-mode imaging using the imaging transducer to transmit and then receive. Proper alignment of the focal point and the tissue to be treated ensures proper positioning of the therapy transducer relative to the patient.

13 Claims, 3 Drawing Sheets

FOCUSED ULTRASOUND SURGERY SYSTEM GUIDED BY ULTRASOUND IMAGING

FIELD OF THE INVENTION

This invention relates to a system for enabling medical procedures to be performed by ultrasonic heating and, more particularly, to a system for enabling selective heating of tissue guided by medical imaging.

BACKGROUND OF THE INVENTION

High-intensity focused ultrasound was proposed many years ago as a method to apply localized thermal energy to living tissue, to cause necrosis in the volume of tissue being treated. In conjunction with such ultrasound surgery system, a system for localizing the tissue volume to be treated prior to applying therapeutic levels of ultrasound energy is needed.

One technique for localizing the tissue volume to be treated is magnetic resonance imaging (MRI), which provides the radiologist with internal views of a patient's anatomy. Magnetic resonance imaging provides excellent contrast between different tissues and is useful in planning surgical procedures. A tumor in a patient is much more visible in an MR image than as seen in actual surgery because the tumor and normal tissue often look similar in surgery. The tumor can also be obscured by blood during surgery.

Tumors have been selectively destroyed in cancer patients using focused ultrasound heating at the University of Arizona, as reported by Billard et al. in: "Effects of Physical Parameters on High Temperature Ultrasound Hyperthermia", Ultrasound in Med. & Biol., Vol. 16, No. 4, pp. 409–420 (1990). The patient is first scanned in an MRI system to locate the tumor and plan a safe trajectory between the entry and target points. A view of the heated region is provided with the use of MR temperature-sensitive pulse sequences. Known MR temperature-sensitive pulse sequences are described in U.S. Pat. No. 4,914,608 to LeBihan et al. entitled "In-Vivo Method for Determining and Imaging Temperature of an Object/Subject from Diffusion Coefficients Obtained by Nuclear Magnetic Resonance". Experiments on animals show that heating a zone of tissue above a critical temperature destroys the tissue. This zone increases in size with time as heat is applied to reach a steady state of both temperature and heat flow. If the maximum temperature is limited to 100° C., then the heated zone, i.e., the area of tissue exceeding a critical temperature so as to undergo tissue destruction, approaches 1 cm in diameter. It is difficult to predict the heated zone geometry because the heat flow depends on the perfusion of blood as well as the tissue thermal properties.

In addition, it is difficult to determine the location of the ultrasound energy focal point without activating the energy transducer. Thus there is need for a method of selectively destroying tissue noninvasively without affecting adjacent healthy tissue.

Ultrasound imaging has been used in high-intensity focused ultrasound therapy systems as a method of localizing tissue to be treated. However, because ultrasound B-mode imaging methods used in imaging are not significantly temperature sensitive, treatment position cannot be verified by imaging until necrosis has actually occurred so as to cause tissue density changes that can be visualized by ultrasound B-mode imaging. Assumptions may be made about where the therapy beam is placed in tissue based on geometric relationships between the imaging transducer and the therapy transducer, but this does not account for the possibility of reflection or refraction which could distort or misregister the placement of therapy regions. Other problems can occur if air bubbles or other objects occlude the acoustic path of the therapy device but not the imaging device. Thus there is need for a system which localizes and verifies the actual position of the high-intensity focused ultrasound beam by imaging tissue using a large-aperture therapy transducer as the transmit element and receiving with a separate receive transducer, such as a single crystal or a series of concentric annular arrays, which are mechanically steered, or a phased array, linear array or curved array, which are electronically steered and focused.

SUMMARY OF THE INVENTION

Focused ultrasound has been demonstrated as an effective means of applying thermal energy to living tissue for therapeutic effect, and has been used in hyperthermia treatments by raising tissue temperature a few degrees. The present invention employs highly focused ultrasonic fields with much higher intensities that quickly produce coagulation necrosis. The tissue temperature in a small localized region is raised to 60°–80° C., thermally destroying the cells in that localized region.

According to the invention, a system and method for employing ultrasound imaging localizes the tissue volume to be treated prior to applying therapeutic levels of ultrasound energy. The system comprises a first transducer capable of producing ultrasonic fields of sufficiently high intensity to cause necrosis, and a second transducer capable of producing high-quality ultrasound images for localization and monitoring. Although one transducer could be used for both therapy and imaging, the preferred embodiments of the invention use separate devices.

In phased-array or linear-array ultrasound B-mode imaging, each image frame is produced by transmitting an ultrasonic beam at a particular position or beam angle and then receiving the echoes from that same direction. The beam angle or position is then incremented and the transmitting and receiving steps are repeated for a particular field of view.

In accordance with a preferred embodiment of the invention, a system for providing thermal therapy employs an imaging array operating in a standard B-mode configuration that can image a full field of view and provide adequate resolution and image quality to identify a tissue region for thermal therapy. The system is also operable in a second mode where image frames are produced by transmitting a beam from a separate therapy transducer (e.g., fixed or annular array) and using the separate imaging transducer (e.g., linear, phased or curved array) to receive as in normal B-mode ultrasonic imaging. For each vector in the frame, a beam is transmitted at a fixed angle and a highly focused depth. Each vector is received at the normal set of angles or the full field of view. This produces image frames where the echoes from the angle and focus depth of the therapy transducer are significantly higher than from the surrounding angles and depths. These image frames show a distinct elliptical region coincident with the focus region of the transmit therapy transducer.

The system is operable in a scanning mode whereby the two frame modes (i.e., standard B-mode and the aforementioned second mode) are interleaved, so the system operator sees normal-looking ultrasound images with a brighter elliptical region at the location of focus of the therapy transducer.

The probe is then manipulated to place this elliptical focus region at the location of the tissue to be thermally treated. When this registration has been made, the system enters a therapy mode wherein significantly higher power is applied to the therapy transducer, which delivers this highly focused energy to the tissue treatment region. Periodically during the therapy mode, short gaps in treatment can be introduced in order to allow normal B-mode image frames to be acquired to verify that registration is maintained and to monitor changes in tissue properties due to the treatment.

The invention is also applicable to pulsed or continuous wave Doppler imaging, particularly for the purpose of impinging the therapy beam on a blood vessel. The position of the target blood vessel is determined by detecting the Doppler phase shift caused by the blood movement. In the high-power mode, the therapy beam can be used to occlude an internally bleeding vessel or stop the flow of blood to a tumor region by thermal coagulation.

BRIEF DESCRIPTION OF THE DRAWINGS

The features of the invention believed to be novel are set forth in the appended claims. The invention, however, together with further objects and advantages thereof, may best be understood by reference to the following description taken in conjunction with the accompanying drawing(s) in which:

DETAILED DESCRIPTION OF THE PREFERRED EMBODIMENTS

Figure 1:
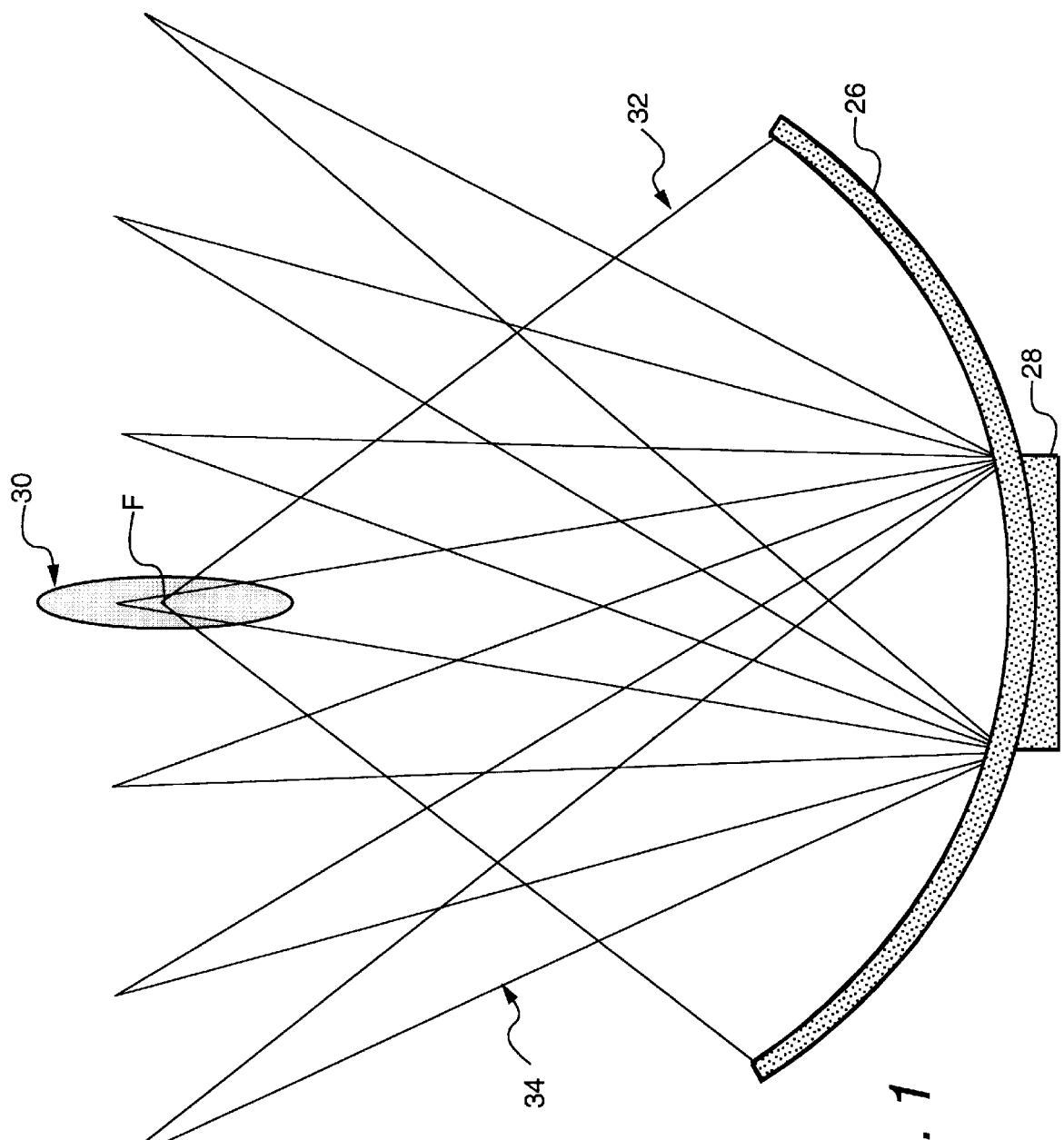
FIG. 1 is a schematic illustration depicting the probe of a focused ultrasound surgery system guided by a phased-array ultrasound imager in accordance with a preferred embodiment of the invention.

In accordance with one preferred embodiment of the invention, a volume of tissue is imaged using a modified conventional B-mode ultrasound imager wherein the probe, as shown in FIG. 1, comprises a spheroidal piezoelectric element 26 (hereinafter "therapy transducer") with a phased-array imaging transducer 28, comprising a multiplicity of piezoelectric elements, mounted in the center. The probe is mounted in a mechanical positioning system (not shown) having three or more axes of motion in a container of an acoustic medium, e.g., water. In particular, therapy transducer 26 can be moved to focus on different locations in the patient. The therapy transducer is focused onto the tumor tissue, avoiding bone or air in the path of the ultrasound beam, and pulsed to selectively heat the tumor tissue at the focal point F of the therapy transducer.

The phased-array transducer 28 constitutes part of a conventional ultrasound imaging system. Such transducers typically comprise an array of ultrasonic transducer elements which transmit an ultrasound beam and then receive reflected ultrasound from an object or target region being studied. For ultrasound imaging, the array typically is made up of a plurality of transducer elements arranged in a line and driven with separate voltages. By selecting the time delay (or phase) and amplitude of the applied voltages, the individual transducer elements can be controlled to produce ultrasonic waves which combine to form a composite or net ultrasonic wave that travels along a preferred vector direction and is focused at a selected point along the beam. Multiple firings may be used to acquire data representing the same anatomical information. The beamforming parameters of each of the firings may be varied to provide a change in maximum focus or otherwise change the content of the received data for each firing, e.g., by transmitting successive beams along the same scan line with the focal point of each beam being shifted relative to the focal point of the previous beam. By changing the time delay and amplitude of the applied voltages, the focal point of the beam can be moved in a plane to scan the target region.

The same principles apply when the transducer is employed to receive the reflected sound (receive mode). The voltages produced at the receiving transducer elements are summed so that the net signal is indicative of the ultrasound reflected from a single focal point in the object. As with the transmission mode, this focused reception of the ultrasonic energy is achieved by imparting separate time delay (and/or phase shifts) and gains to the signal from each receiving transducer element.

Ultrasound beam scanning as described above comprises a series of measurements in which the steered ultrasonic wave is transmitted, the system switches to its receive mode after a brief time interval, and the reflected ultrasonic wave is received and stored. Typically, transmission and reception are steered in the same direction during each measurement to acquire data from a series of points along an acoustic beam or scan line. The receiver is dynamically focussed at a succession of ranges along the scan line as the reflected ultrasonic waves are received.

The positioning system for moving the focal point F of the probe to a desired location allows multiple two-dimensional B-mode images to be acquired by a work-station as a registered set of image slices representing a tissue volume. The imaging volume can then be reformatted as necessary to obtain the views desired. Since the registration of the object (i.e., patient) is fixed to the mechanical positioning system, the probe can be registered to the positioning system. This provides a known mechanical relationship between the probe and the patient. The system operator can then prescribe the tissue volume to be treated by outlining tissue boundaries on a set of ultrasound image slices describing a tissue volume including the tissue volume to be treated. The combined imaging and therapy probe can then be moved by the positioning system to locations within the prescribed outline to deliver treatment to the desired area of each image slice.

At each treatment location, prior to delivery of the therapy, verification of the therapy beam location is accomplished by way of ultrasound B-mode imaging using therapy transducer 26 as the ultrasound emitter and phased-array imaging transducer 28 as the detector. In a transmit mode, therapy transducer 26 is pulsed to produce a transmit field 32 which is focused at point F. In a receive mode, the elements of phased-array imaging transducer 28 are time-delayed to form successive receive beams 34. This provides a B-mode image wherein the only area in the image to be significantly illuminated is at the focus F of therapy transducer 26. This yields an image with an elliptical artifact 30 related to the position and amplitude of the pulse applied to the therapy element. These image frames can then be interleaved with, or superimposed on, normal B-mode imaging frames where both transmit and receive functions are performed using only phased-array imaging transducer 28. Once the therapy treatment location has been verified in this manner, therapy can be delivered by applying higher-power, longer-duration excitation to the large therapy element 26.

The intended use for the invention is to provide a system and method for identifying and localizing tissue volumes to be treated, prescribing tissue to be treated, and applying significant thermal energy to a localized tissue region due to ultrasonic absorption, while verifying each position to avoid errors due to reflection, refraction, or mechanical positioning errors.

Figure 2:
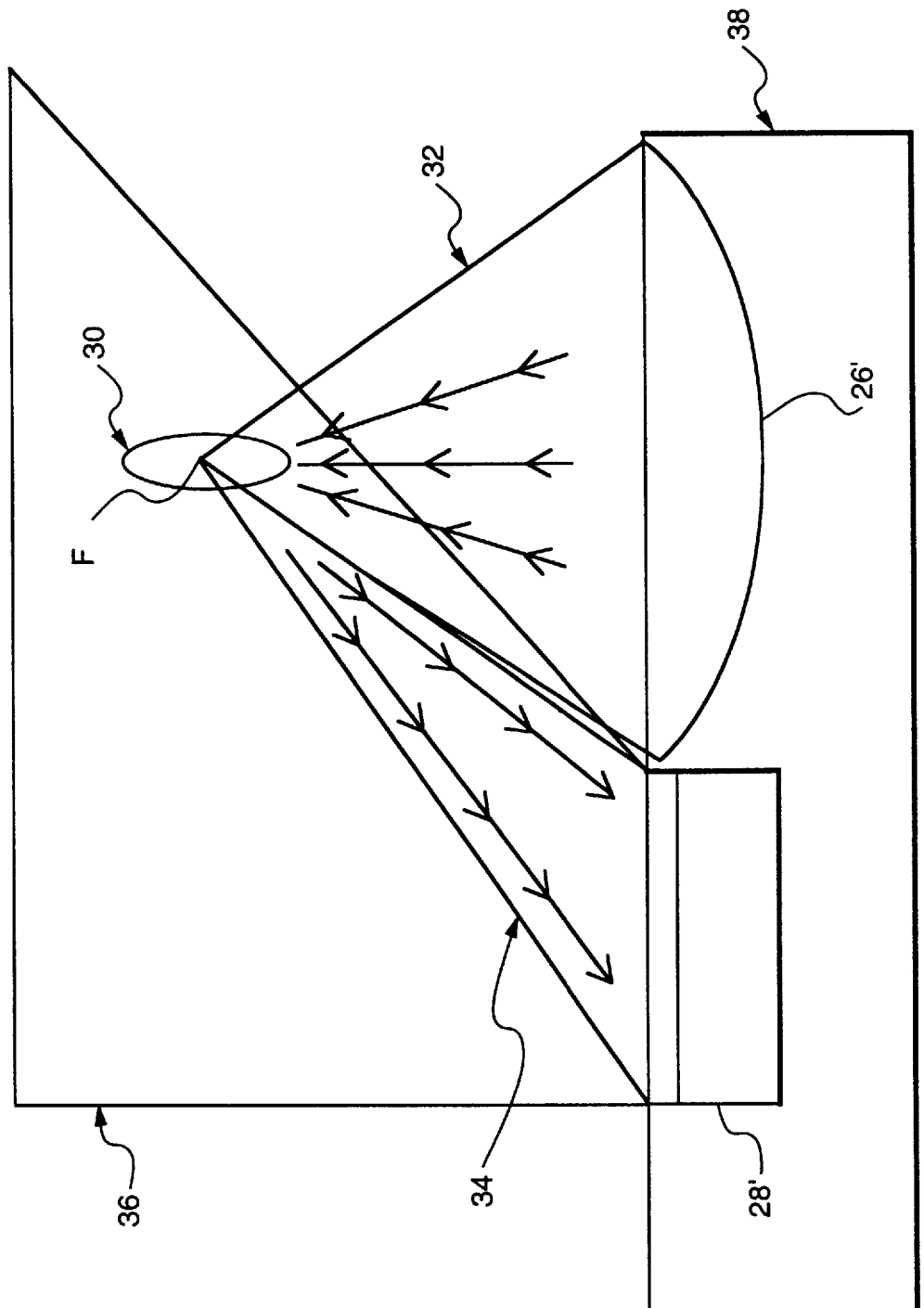
FIG. 2 is a schematic illustration depicting the probe of a focused ultrasound surgery system guided by a phased-array ultrasound imager in accordance with an alternative preferred embodiment of the invention.

In the alternative preferred embodiment depicted in FIG. 2, instead of the phased-array imaging transducer being incorporated into the therapy transducer, a spheroidal therapy transducer 26' and a phased-array imaging transducer 28' are rigidly mounted on a positioning system 38 in fixed relationship, one laterally displaced from the other. In this embodiment, the B-mode imaging field for phased-array transducer 28' is designated 36, the transmit field for therapy transducer 26' is designated 32, and the receive beam for phased-array transducer 28' when therapy transducer 26' is used as the transmitter is designated 34. Using therapy transducer 26' to transmit and phased-array imaging transducer 28' to receive yields an image with an elliptical artifact 30 related to the position and amplitude of the pulse applied to the therapy transducer. As described previously, these image frames can then be interleaved with, or superimposed on, normal B-mode imaging frames where transmit and receive functions are performed using only phased-array imaging transducer 28'. The position of the transducers can then be adjusted until elliptical artifact 30 is registered with the portion of the displayed B-mode image corresponding to the tissue to be heated.

Figure 3:
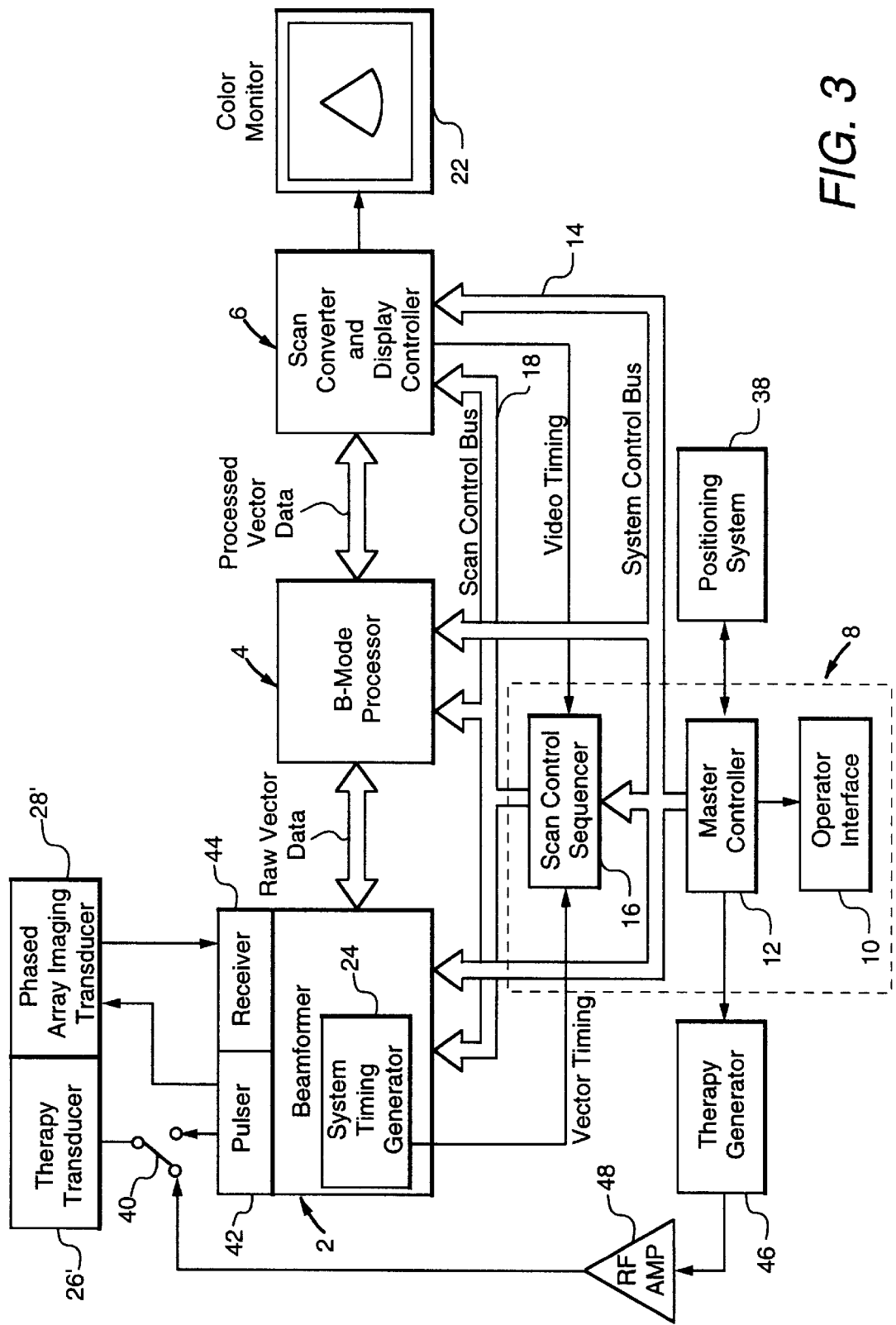
FIG. 3 is a block diagram of a focused ultrasound surgery system guided by a phased-array ultrasound imager in accordance with the alternative preferred embodiment of the invention.

FIG. 3 depicts a focused ultrasound surgery system guided by a phased-array ultrasound imager in accordance with the preferred embodiments of FIG. 1 and FIG. 2. The ultrasound imaging system includes four main subsystems: a beamformer 2, a B-mode processor 4, a scan converter and display controller 6 and a kernel 8. System control is centered in the kernel, which accepts operator inputs through an operator interface 10 and in turn controls the various subsystems. A master controller 12 performs system level control functions by accepting inputs from the operator via operator interface 10 as well as system status changes (e.g., mode changes) and making appropriate system changes either directly or via a scan control sequencer. A system control bus 14 provides an interface between the master controller and the subsystems. Scan control sequencer 16 provides real-time (acoustic vector rate) control signals to beamformer 2 including a system timing generator 24, and to B-mode processor 4 and scan converter 6. Scan control sequencer 16 is programmed by the host with the vector sequences and synchronization options for acoustic frame acquisitions. The scan converter broadcasts the vector parameters defined by the host to the subsystems via scan control bus 18.

The main data path begins with the analog RF (radio frequency) input signals to receiver 44 from phased-array imaging transducer 28'. Beamformer 2 produces raw vector data beams that are supplied to B-mode processor 4, where they are processed and supplied as vector (beam) data to scan converter and display processor 6. The scan converter and display controller accepts the processed vector data and produces video display signals for the image to a color monitor 22.

Beamformer 2 is responsible for the transmit and receive beamforming. Each transducer includes an array of separately driven transducer elements, each of which produces a burst of ultrasonic energy when energized by a pulsed waveform produced by a transmitter or pulser 42. The ultrasonic energy reflected back to the transducer array from the patient under study is converted to an electrical signal by each receiving transducer element and applied separately to respective analog receiver channels in receiver 44 through a set of transmit/receive (T/R) switches (not shown). Pulser 42, receiver 44 and the T/R switches are operated under control of a front end controller (not shown) in beamformer 2. A complete B-mode scan is performed by acquiring a series of echoes in which the T/R switches are set to their transmit positions, pulser 42 is gated ON momentarily to energize each transducer element, the T/R switches are then set to their receive positions, and the subsequent echo signals produced by each transducer element are applied to the respective receiver channels of receiver 44.

The location of the focal point of pulsed therapy transducer 26' is not imaged by conventional B-mode imaging. Instead, therapy transducer 26' is operable in both an imaging mode and a therapy mode so that, in the imaging mode, the therapy transducer is pulsed by pulser 42 to produce a transmitted relatively low-energy beam focused at focal point F (see FIG. 2). Phased-array imaging transducer 28' is then steered to scan the patient's tissue, thereby acquiring receive beams including ultrasound scattered from the tissue at the focal point of the pulsed therapy transducer. This scattered ultrasound from the tissue at the focal point allows the position of the fixed-focus therapy transducer to be detected and imaged. The image of the focal point can then be superimposed on an image of the tissue to be treated, obtained by conventional B-mode imaging using the phased-array imaging transducer, as previously described.

In response to any difference between the detected location of the therapy transducer focal point and the detected location of the tissue to be treated, the position of the probe is adjusted using positioning system 38 which is mechanically coupled to the probe. The necessary adjustment is done automatically under the control of master controller 12. Alternatively, the adjustment can be made by manual operation of the positioning system.

When the probe is in the correct position relative to the tissue to be treated, therapy transducer 26' is switched to the therapy mode by operation of a switch 40. In the therapy mode, master controller 12 actuates a therapy generator 46 to produce an electrical pulse of energy and duration sufficient to excite the therapy transducer to emit ultrasound having a desired therapeutic level at its focal point. The electrical pulse from therapy generator 46 is amplified by a radio-frequency amplifier 48 and then supplied to the therapy transducer through switch 40. As a result, ultrasound energy at a therapeutic level is applied at focal point F (FIG. 2) corresponding to the location of the tissue to be treated.

While only certain preferred features of the invention have been illustrated and described, many modifications and changes will occur to those skilled in the art. It is, therefore, to be understood that the appended claims are intended to cover all such modifications and changes as fall within the true spirit of the invention.

What is claimed is:

1. A method for employing ultrasound imaging to guide focused ultrasound surgery, comprising the steps of:

positioning a probe, including an ultrasonic therapy transducer and an ultrasonic imaging transducer, relative to a patient such that a focal point of the therapy transducer is located in tissue of the patient, said transducers being in fixed positional relationship to each other;

operating said imaging transducer in transmit and receive modes to acquire data sufficient to form an image of tissue to undergo necrosis;

displaying an image of said tissue to undergo necrosis;

applying relatively low electrical energy to said therapy transducer, said relatively low electrical energy having an amplitude and duration to cause ultrasound energy to be transmitted by said therapy transducer to the focal point at a level that is insufficient to cause necrosis of tissue at the focal point;

operating said imaging transducer in the receive mode to acquire data sufficient to form an image of an artifact representing ultrasound energy scattered by the tissue at said focal point in response to application of said relatively low electrical energy to said therapy transducer;

displaying an image of said artifact; and registering said image of said artifact relative to said image of said tissue to undergo necrosis.

2. The method of claim 1 and further comprising the step of applying relatively high electrical energy to said therapy transducer when said artifact and images indicate that said focal point is located at said tissue to undergo necrosis, said relatively high electrical energy having an amplitude and duration to cause ultrasound energy to be transmitted by said therapy transducer to the focal point at a level that is sufficient to cause necrosis of the tissue at the focal point.

3. The method as defined in claim 1 and further comprising the steps of:

determining the position of said artifact relative to said tissue to undergo necrosis;

adjusting the probe position relative to the patient until said artifact coincides with said tissue to undergo necrosis; and applying relatively high electrical energy to said therapy transducer, said relatively high electrical energy having an amplitude and duration to cause ultrasound energy to be transmitted by said therapy transducer to the focal point at a level that is sufficient to cause necrosis of the tissue at said focal point.

4. A method for employing ultrasound imaging to guide focused ultrasound surgery, comprising the steps of:

positioning a probe, including an ultrasonic therapy transducer and an ultrasonic imaging transducer, relative to a patient such that a focal point of the therapy transducer is located in tissue of the patient, said transducers being in fixed positional relationship to each other;

applying relatively low electrical energy to the therapy transducer, said relatively low electrical energy having an amplitude and duration such that ultrasound energy transmitted by the therapy transducer to the focal point in response thereto is insufficient to cause necrosis of tissue at the focal point; and controlling a plurality of elements of the imaging transducer to form a receive beam of ultrasound energy scattered by the tissue at the focal point in response to application of said relatively low electrical energy to the therapy transducer.

5. The method of claim 4 and further comprising the step of applying relatively high electrical energy to the therapy transducer after the step of controlling a plurality of elements of the imaging transducer, said relatively high electrical energy having an amplitude and duration such that ultrasound energy transmitted by the therapy transducer to the focal point in response thereto is sufficient to cause necrosis of tissue at the focal point.

6. The method of claim 4 wherein the step of controlling a plurality of elements of the imaging transducer comprises the steps of:

controlling a plurality of elements of the imaging transducer to form a transmit beam of ultrasound energy directed at tissue to be treated;

controlling a plurality of elements of the imaging transducer to form a receive beam of ultrasound energy scattered by the tissue to be treated in response to said transmit beam; and determining the position of said focal point relative to said tissue to be treated.

7. The method of claim 6 and further comprising the steps of:

adjusting the position of the probe relative to the patient after the step of determining the position of said focal point relative to said tissue to be treated, until said focal point coincides with said tissue to be treated; and applying relatively high electrical energy to the therapy transducer, said relatively high electrical energy having an amplitude and duration such that ultrasound energy transmitted by the therapy transducer to the focal point in response thereto is sufficient to cause necrosis of the tissue to be treated.

8. A system for performing focused ultrasound surgery guided by ultrasound imaging, comprising:

a probe including an ultrasonic therapy transducer and an ultrasonic imaging transducer arranged in a predetermined fixed positional relationship to each other;

a pulsing circuit coupled to said imaging transducer;

a receiving circuit coupled to said imaging transducer;

a therapy generator; and means for selectively providing energization to said therapy transducer from either said therapy generator or said pulsing circuit.

9. The system of claim 8, wherein said therapy transducer comprises a spheroidal piezoelectric element.

10. The system of claim 8, wherein said imaging transducer is situated at the center of said spheroidal piezoelectric element.

11. The system of claim 8, wherein said imaging transducer is situated outside said spheroidal piezoelectric element.

12. The system of claim 8 and further comprising a positioning system mechanically linked to said probe for moving said probe relative to a stationary target.

13. The system of claim 8 and further comprising a display monitor, and a processor for forming an image on said display monitor in response to receipt by said imaging transducer of scattered ultrasound energy.

* * * * *